United States Patent [19]

Aizenman et al.

[11] Patent Number: 5,145,862
[45] Date of Patent: Sep. 8, 1992

[54] METHOD OF RESISTING NEURODEGENERATIVE DISORDERS

[75] Inventors: Elias Aizenman, Pittsburgh, Pa.; Paul A. Rosenberg, Newton; Paul M. Gallop, Chestnut Hill, both of Mass.

[73] Assignee: University of Pittsburgh of the Commonwealth System of Higher Education, Pittsburgh, Pa.

[21] Appl. No.: 758,576

[22] Filed: Sep. 12, 1991

Related U.S. Application Data

[62] Division of Ser. No. 568,301, Aug. 16, 1990, Pat. No. 5,091,391.

[51] Int. Cl.$^5$ .......................................... A61K 31/415
[52] U.S. Cl. ...................................................... 514/398
[58] Field of Search ............................................. 514/398

[56] References Cited

U.S. PATENT DOCUMENTS 4,806,543  2/1989  Choi ................................. 514/464

FOREIGN PATENT DOCUMENTS 0262345  6/1987  European Pat. Off. .

OTHER PUBLICATIONS

Drejer et al., Journal of Neurochemistry, 45:145-151 (1985) Cellular Origin of Ischemia-Induced Glutamate Release from Brain Tissue In Vivo and In Vitro.
Simon et al., Science 226:850-852 (1984) Blockade of N-Methyl-D-Aspartate Receptors May Protect Against Ischemic Damage in the Brain.
Gill, et al., Neuroscience 7:3343-3349 (1987) Systemic Administration of MK-801 Protects Against Ischemia-Induced Hippocampal Neurodegeneration in the Gerbil.
Andine et al., Neuroscience Letters 90:208-212 (1988) The excitatory a amino acid antagonist kynurenic acid administered after hypoxic-ischemia in neonatal rats offers neuroprotection.
Kochhar et al., Arch. Neurol. 45:148-153 (1988) Glutamate Antagonist Therapy Reduces Neurologic Deficits Produced by Focal Central Nervous System Ischemia.
Barnes, Science vol. 239, pp. 254-256 (1988) NMDA Receptors Trigger Excitement.
Hahn et al., Science USA, 85:6556 (1988)-Central mammalian neurons normally nesistant to glutamate toxicity are made sensitive by elevated extracellular $CA^{2+}$: Toxicity is blocked by the N-methyl-D-aspartate antagonist MK-801.
Choi et al., Neuron, 1:623-634 (1988) Glutamate Neurotoxicity and Diseases of the Nervous System.
Choi et al., The Journal of Neuroscience, 7(2):357-368 (1987) Glutamate Neurotoxicity in Cortical Cell Culture.
Choi et al., The Journal of Neuroscience 8(1):185-196 (1988) Pharmacology of Glutamate Neurotoxicity in Cortical Cell Culture:Attenuation by NMDA Antagonists.
Steinberg et al., Stroke 20:1247-1252 (1989) Protective Effect of N-Methyl-D-Aspartate Antagonists After Focal Cerebral Ischemia in Rabbits.
Nowack et al., Nature 307:462-564 (1984) Magnesium gates glutamate-activated channels in mouse central neurones.
Johnson et al., Nature 325:529-531 (1987) Glycine potentiates the NMDA response in cultured mouse brain neurons.
Westbrook et al., Nature 328:640-643 (1987) Micromolar Concentrations of $Zn^{2+}$ Antagonize NMDA and GABA Responses of Hippocampal Neurons.
Peters et al., Science 236:589-593 (1987) Zinc Selectively Blocks the Action of N-Methyl-D-Aspartate on Cortical Neurons.
Ranson et al. J. Neurochem. 51:830-836 (1988) Cooperative Modulation of [$^3$H]MK-801 Binding to the N-Methyl-D-Aspartate Receptor-Ion Channel Complex by L-Glutamate, Glycine, and Polyamines.
Mayer et al., Tins, pp. 59-61 (1987) Cellular mechanisms underlying excitotoxicity.
Gill et al., Neuroscience, 25:847-855 (1988) KM-801 is Neuroprotective in Gerbils When Administered During the Post-Ischaemic Period.
Tecoma et al., Neuron, 2:1541-1545 (1989) Traumatic Neuronal Injury in Vitro is Attenuated by NMDA Antagonists.
Aizenman et al., Neuron, 2:1257-1263 (1989) Selective Modulation of NMDA Responses by Reduction and Oxidation.
Gallop et al., Trends in Biochemical Sciences 14:343-346 (1989) PQQ, the elusive coenzyme.
Killgore, Science, 245:850-852 (1989) Nutritional Importance of Pyrroloquinoline Quinone.
Rosenberg et al., Neuroscience Letters, 103:162-168 (1989) Hundred-fold Increase in Neuronal Vulnerability to glutamate toxicity in astrocyte-poor cultures of rat cerebral cortex.
Aizeman et al., Neuroscience Letters 116:168-171 (1990) A 3,4-dihydroxyphenylalanine oxidation product is a non-N-methyl-D-aspartate glutamatergic agonist in rat cortical neurons.
Levy et al., Neuroscience Letters 110:291-296 (1990) Redox odulation of NMDA receptor-mediated toxicity in mammalian central neurons.
Olney et al., Science 244:1360-1362 (1989) Pathological Changes Induced in Cerebrocortical Neurons by Phencyclidine and Related Drugs.

(List continued on next page.)

Primary Examiner—S. J. Friedman
Attorney, Agent, or Firm—Arnold B. Silverman

[57] ABSTRACT

A method of resisting neurological damage caused by overstimulation of the NMDA receptor of nerve cells by glutamate includes exposing the NMDA receptors to an oxidizing agent to thereby diminish overall activity of the receptors following activation by glutamate. The oxidizing agent preferably is a material selected from the group consisting of pyrroloquinoline quinone and topa hydantoin.

15 Claims, No Drawings

OTHER PUBLICATIONS

Watanabe et al., Protective Effect of Pyrroloquinoline Quinone Against Experimental Liver Injury in Rats, Current Therapeutic Research, vol. 44, No. 6, Dec. 1988.

Watanabe et al., Nephrotoxicity of Pyrroloquinoline Quinone in Rats Hiroshima J. Med. Sci., vol. 38, No. 1, 49–51, Mar. 1989 HIJM38-9.

Nishigori et al., Preventive Effects of Pyrroloquinoline Quinone on Formation of Cataract and Decline of Lenticular and Hepatic Glutathione of Developing Chick Embryo After Glucocorticoid Treatment, Life Sciences, vol. 45, pp. 593–598 (1989).

Hobara et al., Quinone Derivatives Lower Blood and Liver Acetaldehyde but Not Ethanol Concentrations Following Ethanol Loading to Rats, Pharmocology 37:264–267 (1988).

Honey et al., Ketamine and Phencyclidine Cause a Voltage-Dependent Block of Responses to L-Aspartic Acid, Neuroscience Letters, 61(1985) 135–139 Elsevier Scientific Publishers Ireland Ltd.

Lawren, A New Piece in the Aging Puzzle, Longevity, Jul. 1990, pp. 35–37.

METHOD OF RESISTING NEURODEGENERATIVE DISORDERS

The invention described herein was made in the course of work supported in part by Public Health Service, Grant No. DA04975 from the National Institutes of Health, National Institute on Drug Abuse. The Government has certain rights in this invention.

This is a division of application Ser. No. 568,301, filed Aug. 16, 1990, now U.S. Pat. No. 5,091,391.

BACKGROUND OF THE INVENTION

1. Field of the Invention

This invention relates to a method for resisting damage to brain cells resulting from excess stimulation of the NMDA receptors thereof by glutamate and, more specifically, it relates to a method for accomplishing this in vivo without exposing the subject to meaningful untoward side effects.

2. Description of the Prior Art

Neurodegenerative disorders such as stroke (ischemia), for example, may cause death or permanent impairment. Progressive nerve cell impairment may be caused by a number of means including ischemia, anoxia, trauma, and exposure to environmental or occupational neurotoxic agents.

Nerve cells in the human brain communicate with each other through chemical signals. The excitatory chemical signal is effected by release of glutamate, which is an amino acid. The cells receiving these signals have receptors. With respect to glutamate, such cells have three main types of excitatory amino acid receptors. These are kainate, quisqualate, and N-Methyl-D-Aspartate (NMDA). Excess quantities of glutamate are potentially toxic to such nerve receptors and can damage the same. It has been found that in certain conditions such as ischemia, nerve cells die because of overstimulation by glutamate of the NMDA receptors. (These receptors are known as "NMDA receptors" as N-Methyl-D-Aspartate is a more effective agonist in this particular glutamate receptor at the other types of glutamate receptors). An analysis of the origin of ischemia-induced glutamate release from brain tissue is contained in Drejer, et al Journal of Neurochemistry, Vol. 45, Pages 145-151 (1985).

In this situation, the glutamate is considered an agonist, i.e., a material that can directly activate a receptor. It has been known to use antagonists to counteract the effect of an agonist on a nerve cell receptor. In essence, the antagonists may be considered as binding to the receptor and displacing the agonist thereby resisting the undesired damage. See generally, co-pending United States patent application Ser. No. 395,396, filed Aug. 17, 1989 and Simon et al. Science 226:850-852 (1984), Gill et al J. Neuroscience 7: 3343-3349 (1987), Andine et al. Neuroscience Letter 90:208-212 (1988), Kochhar et al. Arch. Neurol. 45:148-153 (1988).

It has previously been suggested that overstimulation of the NMDA receptors may cause nerve cell death in heart attack or stroke patients. See Barnes, Science Vol. 239 pp. 254-256 (1988). See also Hahn et al., Science USA, 85:6556 (1988).

In respect of the abnormal activation of glutamate receptors specific for the synthetic analogue, NMDA has been indicated as contributing to progressive neurodegenerative disorders. See Choi et al., Neuron, Vol. 1, Pages 623-634 (1988); Choi et al., The Journal of Neuroscience, 7(2):Pages 357-368 (1985); and Choi et al. The Journal of Neuroscience 8(1):Pages 185-196 (1988).

U.S. Pat. No. 4,806,543 discloses a method of reducing adverse effects of neurotoxic injury by administering an enantiomer of an analgesic opioid agonist or antagonist. The compounds are said to be useful for treatment of animal species having NMDA receptors.

It has been suggested that selected antagonism of NMDA receptors can reduce hypoxic ischemic neuronal injury. See Steinberg et al., Stroke, Vol. 20., No. 9, Page 1247-1252 (1989).

Co-pending United States patent application Ser. No. 395,396 discloses a class of simple amino acids which are derivatives of topa quinone, a potent glutamate agonist acting at non-NMDA (i.e., kainate or quisqualate) receptors. Topa quinone was found to be a good oxidizing agent acting at NMDA receptor redox modulatory sites. Topa quinone, however, is neurotoxic and it is highly unstable in solution.

Among such suggested materials are magnesium (Nowack et al. Nature 307:462-564 (1984)); glycine (Johnson et al. Nature 325:529-531 (1987)); zinc (Westbrook et al. Nature 328:640-643 (1987)); (Peters et al. Science 236:589-593 (1987)); and polyamines, (Ransom et al. J. Neurochem. 51:830-836 (1988)). See also the reference to use of phencyclidine and ketamine, as well as 2-amino-7 phosphonohep tanoic acid (AP7) all suggested as NMDA receptor specific antagonists in Mayer et al. Tins Pages 59-61 (1987).

It is also been suggested that the drug (+ − 5-methyl-10, 11-dihydro-5H-dibenzo [a,d]cyclohepten-5,10-imine maleate (MK-801) may provide neuroprotective effects in respect of the NMDA receptors. See Gill et al., Neuroscience, Vol. 25, No. 3, Pages 847-855 (1988).

It is also been known that traumatic neuronal injury may contribute to neuronal degeneration which may be reduced by an NMDA antagonist. See Tecoma et al., Neuron, Vol. 2, Pages 1541-1545 (1989).

Modulation of NMDA responses by reduction and oxidation as by using sulfhydryl redox reagents dithiothreitol (DTT) and 5-5-dithio-bis-2-nitrobenzoic acid (DTNB) NMDA responses has been considered in Aizenman et al. Neuron, Vol. 2, Pages 1257-1263 (1989). Regulation of NMDA function by reduction or oxidation is suggested.

In spite of the recognition of the problem and efforts to employ means to block the consequences of abnormal activation of glutamate on NMDA, there remains a very real and substantial need for an improved method for both preventative measures and therapeutic measures so as to resist the adverse consequences of neurodegenerative disorders.

SUMMARY OF THE INVENTION

The present invention has met the above-described need by providing a method of resisting neurological damage caused by overstimulation of the NMDA receptor by glutamate. This is accomplished by exposing the receptors to an effective dosage of an oxidizing agent to decrease the activity of NMDA receptors activated by glutamate. This is preferably accomplished by using a material selected from the group consisting of pyrroloquinoline quinone and topa hydantoin. These materials serve to effect a change in the NMDA receptor through oxidation.

The NMDA receptor is believed to contain one or more vicinal sulfhydryl groups which are exposed to the extracellular milieu. Oxidation of these sulfhydryl groups (i.e., conversion to a disulfide bond) decreases the overall state of activation of the NMDA receptor such that glutamate will still bind to the receptor, but the cellular response will be diminished. Pyrroloquinoline quinone and topa hydantoin can oxidize such sulfhydryl groups into a disulfide bond.

The oxidation agent is selected so as to have an effective dosage while not being toxic to the subject in such dosage.

It is an object of the present invention to provide an effective means of resisting neurological damage to neurons that may occur due to overstimulation of NMDA receptors resulting from neurological disorders.

It is a further object of the present invention to administer NMDA receptor oxidation agents in high-risk individuals prior to their developing a stroke or other neurodegenerative disorder.

It is further object of this invention to provide such a method which is safe to employ and effective even after the onset of attack on nerve cells as a result of such disorders.

It is a further object of this invention to provide such a method which avoids undesired side effects, such as toxicity.

These and other objects of the invention will be more fully understood from the following description.

DESCRIPTION OF THE PREFERRED EMBODIMENTS

As used herein, "subject" means a member of the animal kingdom including human beings.

As used herein, "neurodegenerative disorder" means a physical condition which has caused or may cause degradation of portion of a subject's nervous system, and shall expressly included, but not be limited to such conditions caused by trauma, a genetic predisposition, and other causes or diseases including, but not limited to stroke, Alzheimer's disease, Parkinson's disease, Huntington's disease, amiotrophic lateral sclerosis, anoxia, and other similar diseases and epilepsy.

As used herein "patient" means a member of the animal kingdom, including human beings who either has or is suspected of having a neurodegenerative disorder.

The present invention contemplates a method of resisting neurological damage due to excessive production of glutamate by the brain and transmission of the same to the NMDA receptor of a central nervous system cell.

The preferred method of the present invention involves administering a non-toxic effective dosage of an oxidizing agent to diminish NMDA receptor activation.

The preferred material for use in this manner is pyrroloquinoline quinone (methoxatin) which is a bacterial redox coenzyme which may readily be synthesized in a manner well known to those skilled in the art. See generally, Gallop et al., Trends in Biochemical Sciences, 14:343-346, 1989, Pages 343-346. Kilgore, Science, Vol. 245, Pages 850-852 (1989) indicates that pyrroloquinoline quinone may be an important growth factor or vitamin. While this material has been recognized as providing certain nutritional benefits in rodents, it is not believed to have been suggested to be used as an oxidizing agent in minimizing neuronal damage via activation of the NMDA receptor in humans.

It is currently believed that NMDA receptor oxidation which results from administering the pyrroloquinoline quinone material to a subject in accordance with this invention occurs through the conversion of vicinal sulfhydryl residue on the NMDA receptors extracellular surface to disulfide bonds.

One of the advantages of pyrroloquinoline quinone is that it can be provided in therapeutically effective dosages without having meaningful undesired side effects such as toxicity. One of the problems with a number of other materials such as MK 801, for example, which have been attempted to be used to block NMDA reception of excess glutamate is they produce a large variety of undesirable side effects including toxicity and, as a result, cannot be used in human patients and, perhaps, are not suitable for the same reason for animal patients. Others involve a delicate balance between efficacy and toxicity and, as a result, are not suitable. With this material it is easy to maintain a desired therapeutic ratio, i.e., the ratio of amount of therapeutic activity to amount of toxicity.

Another oxidizing agent usable in the method of the present invention is topa hydantoin which is a stable, non-toxic topa derivative.

It will be appreciated, therefore, that the invention involves administering a non-toxic therapeutically effective dosage of a material selected from the group pyrroloquinoline quinone, and topa hydantoin.

The oxidizing agent may preferably be administered orally although other a suitable means known to those skilled in the art may be employed. Depending upon the dosage form selected, suitable inert vehicles, buffering agents, binding agents, and the like, well known to those skilled in the art, may be employed.

Those skilled in the art will know how to determine, by routine experimentation, the amount and frequency of administration of oxidizing agent necessary to provide sufficient resistance to neuronal damage via the NMDA receptor without employing a toxic level or potentially toxic level of the oxidizing agent.

With respect to subjects who are not "patients" as defined herein, those at risk may be determined by routine screening to ascertain whether they have an abnormally high level of glutamate or related compounds in the central nervous system, and also those who have a genetic predisposition to the development of diseases, which have been linked to overstimulation of the NMDA receptors, e.g. Huntington's Disease.

It will be appreciated, therefore, that not all oxidizing agents may be employed in the practice of this invention because some agents such as DTT and DTNB would tend to be too toxic to have any practical application. Other problems can make oxidizing agents unsuitable. For example, topa quinone although a good oxidizing agent is excitotoxic via non-NMDA receptor activation, it may not oxidize the NMDA receptors and is quite unstable as it breaks down in solution. The derivative, topa hydantoin, does not have this shortcoming.

In order to confirm that pyrroloquinoline quinone was able to oxidize the NMDA receptor, both electrophysiological and toxicity tests were performed.

EXAMPLE I

In the electrophysiological tests, whole cell voltage-clamp recordings were performed on rat cortical neurons in vitro using the procedure set forth in Aizenman et al., Neuron, Vol. 2, Pages 1257-1263 (1989). It was observed that pyrroloquinoline quinone (5 micromolar)

was able to initiate and at least partially effect reversal of the potentiating actions that two millimolar DTT had on NMDA induced currents.

EXAMPLE II

Toxicity assays were performed in accordance with Rosenberg et al., Neuroscience Letters, Vol. 103, Pages 162-168 (1989). A 5 minute exposure to 50 micromolar pyrroloquinoline quinone was sufficient to resist significant NMDA receptor mediated toxicity in rat cortical neurons in vitro. The pyrroloquinoline quinone was not toxic to neurons, even when present for a test period of 24 hours.

It is believed that the action of pyrroloquinoline quinone on the NMDA receptor is probably mediated by oxidation of a redox modulatory site on the NMDA receptor. There is likely to be at least one pair of vicinal sulfhydryl groups on the extracellular surface of the NMDA receptor which form said redox modulatory site.

It will be appreciated that the method of the present invention provides a safe and effective means for resisting neural damage via glutamate receptors specific for the synthetic analogue NMDA. All of this is accomplished in a safe, efficient manner which may use known oxidizing agents which are not neurotoxic. The oxidation reaction, unlike the drug blocking action, accomplishes this phenomenon in the following way. Glutamate may still bind to its receptor, but the activity of the receptor is diminished.

A non-competitive blocker such as MK 801 may still bind effectively to its site of action after NMDA receptor oxidation. Therefore, the oxidation site (redox modulatory site) is distinct from the MK 801 binding site. The redox modulatory site used in the method of the present invention is also distinct from the other sites previously known to modify NMDA receptor function such as the glycine, zinc, magnesium and polyamine sites.

Further, it will be appreciated that by diminishing the NMDA receptor activation during a stroke or other illness, the magnitude of the harm done can be diminished.

While for convenience of reference herein, specific reference has been made frequently to stroke or ischemia, it will be appreciated that the invention is not so limited and that a wide variety of progressive neurodegenerative disorders and other neurodegenerative disorders may be treated beneficially or prevented by the method of the present invention.

Whereas particular embodiments of the invention have been described above for purposes of illustration, it will be evident to those skilled in the art that numerous variations of the details may be made without departing from the invention as defined in the appended claims.

We claim:

1. A method of resisting neurological damage in a subject caused by overstimulation of the NMDA receptors of nerve cells by glutamate comprising,
   administering to said subject an effective dose of the oxidizing agent topa hydantoin to thereby diminish the activity of NMDA receptors after activation by glutamate.

2. The method of claim 1, employing said method on a human being.

3. The method of claim 2, employing said method to treat a patient.

4. The method of claim 3, administering said oxidizing agent orally.

5. The method of claim 4, employing said method to treat a stroke victim.

6. The method of claim 1, employing said method on a subject who is at risk of neurological damage from ischemia or anoxia as a prophylactic measure.

7. The method of claim 1 employing said method on a patient suffering from a neurodegenerative disorder.

8. The method of claim 7,
   administering said oxidizing agent to said patient after an ischemic attack to limit infarct size.

9. The method of claim 1,
   effecting said oxidation at a redox modulatory site of said NMDA receptor.

10. The method of claim 1,
    employing said oxidation to convert sulfhydryl residue on the NMDA extracellular surface to disulfide bonds.

11. A method of resisting neurological damage to neurons by overstimulation on the NMDA receptors of a patient comprising,
    administering to said patient an effective dosage of the oxidizing agent topa hydantoin to diminish NMDA receptor activation.

12. The method of claim 11,
    employing said method to resist glutamate damage via said NMDA receptors.

13. The method of claim 11,
    employing said method on a patient who has had a stroke.

14. The method of claim 11,
    effecting said diminishing of NMDA receptor activation at a redox modulatory site of said receptor.

15. The method of claim 11,
    employing said oxidizing agent to convert vicinal sulfhydryl residue on said NMDA extracellular surface to disulfide bonds.

* * * * *